106-15.05 SR

5/19/87 XR 4,666,747

United States Patent [19]

Quinn

[11] Patent Number: 4,666,747
[45] Date of Patent: May 19, 1987

[54] SPRAY METHOD AND FORMULATION FOR USE THEREIN

[75] Inventor: Peter J. Quinn, Wheatley, England

[73] Assignee: Acacia Chemicals Ltd., London, England

[21] Appl. No.: 765,685

[22] Filed: Aug. 15, 1985

Related U.S. Application Data

[62] Division of Ser. No. 640,981, Aug. 15, 1984, abandoned.

[30] Foreign Application Priority Data

Aug. 15, 1983 [GB] United Kingdom ................ 8321913

[51] Int. Cl.$^4$ ................................ C09D 5/14

[52] U.S. Cl. ................................ 427/421; 106/15.05; 514/65

[58] Field of Search ..................... 106/15.05; 427/421; 514/65

[56] References Cited

U.S. PATENT DOCUMENTS

| | | | |
|---|---|---|---|
| 3,130,121 | 4/1964 | Rapport | 424/186 |
| 4,394,149 | 7/1983 | Szoka et al. | 71/28 |

FOREIGN PATENT DOCUMENTS

| | | |
|---|---|---|
| 0068296 | 5/1983 | European Pat. Off. . |
| 0068294 | 5/1983 | European Pat. Off. . |
| 0068297 | 5/1983 | European Pat. Off. . |
| 528054 | 10/1940 | United Kingdom . |
| 2067406 | 7/1981 | United Kingdom . |
| 2015464 | 8/1982 | United Kingdom . |
| 2110518 | 6/1983 | United Kingdom . |

*Primary Examiner*—Lorenzo B. Hayes
*Attorney, Agent, or Firm*—Merchant, Gould, Smith, Edell, Welter & Schmidt

[57] ABSTRACT

A wettable powder which can be made up into a sprayable aqueous dispersion for use in pest control to allow an active substance to be applied to a surface to be retained thereon for an extended duration, particularly without undergoing degradation of its properties, comprises the active agent which is an active agent not readily soluble in water and a water-soluble naturally occurring organic product such as a phospholipid having the capacity to serve as a non-polar domain which has high affinity for hydrophobic molecules to keep them in a stable aqueous dispersion.

11 Claims, 8 Drawing Figures

SPRAY METHOD AND FORMULATION FOR USE THEREIN

This is a division of application Ser. No. 640,981, filed Aug. 15, 1984, now abandoned.

This invention relates to a spray method for use in agriculture and horticulture, in particular in pest control and to formulations, more particularly wettable powders, for use therein.

In agriculture and horticulture it is necessary to combat a wide variety of pests at different stages of plant growth. These generally require the spraying of cultivated land and/or growing plants with one or more of a variety of pest control agents at appropriate stages of the plant growth cycle or level and type of pest infestation. These pest control agents act according to their constitution as for example fungicides, insecticides, acaricides, nematocides, molluscicides etc. In general these pest control agents are organic compounds and are not soluble in water or like polar solvents. They are therefore usually applied in the form of a water/oil emulsion generally containing a synthetic detergent as emulsifying agent. One such composition is Derris, an extract of the Derris plant root which contains rotenone as the active insecticidal and acaricidal ingredient. The concentration of synthetic detergent must satisfy two mutually exclusive criteria in applications to biological material (a) it must produce a homogeneous and stable emulsion to ensure even application and (b) must be harmless to the living organism. In general, the concentrations safely used in pesticide formulations for application to plants must be so low that they do not produce stable emulsions in water with most organic pesticides. Other undesirable effects associated with the use of synthetic dispersants are that they can facilitate removal of the biologically-active ingredients from plant foliage during weathering (e.g. rain) and they tend to persist and pollute the environment.

Moreover, because of the tendency for wash-off and the short life of a pest control agent on the plant before loss therefrom, if prolonged protection is required, possibly involving protection against different pests at different stages in the life of the plant, then repeated sprayings are generally required.

Controlled release compositions have hitherto been designed to meet a variety of requirements in technology, particularly in the pharmaceutical industry, and generally involve for example the embedding of an active ingredient in a matrix which is slowly eroded or from which the active ingredient is leached. Such tablets or equivalent formulations clearly provide little assistance to the practitioner in agricultural chemistry where the formulation has to be retained on for example leaf surfaces. Also known are encapsulated dyestuffs which are retained on surfaces to which they have been applied and which only liberate their dye to produce the desired colouring effect when subjected to a mechanical process sufficient to break the capsule. Such capsules are used for example in the production of "carbonless" copying paper.

More recently, pharmaceutical compositions have become known which comprise liposomes as the carrier, vector or adjuvant for the biologically active ingredients. The liposomes consist of amphipathic molecules characterised by a polar headgroup separated discretely from non-polar residues in the molecule. These molecules are typified by the phospholipids and glycolipids found as constituents of most biological material. Upon dispersal in polar media e.g. water or dilute aqueous salt solutions these molecules spontaneously form multibilayer structures in which the polar head groups align at the aqueous surface of a lamellar structure and the hydrophobic residues orient into the central region where they exclude solvent molecules and create a hydrophobic domain. With more vigorous dispersal methods e.g. exposure to ultrasound, the multi-lamellar liposomes break down to unilamellar or oligolamellar vesicles in which the ratio of trapped or encapsulated aqueous phase per amphipathic molecule increases. The pharmaceutically active ingredients, in general, are soluble in the aqueous phase and when trapped inside liposome structures have wide and well-documented applications in medicine. To form liposome structures of this type the amphipathic molecules, dried from organic solvent, may be dispersed in aqueous media containing the pharmaceutical compound and the untrapped material removed by dialysis or some other means. Alternatively, the amphipathic molecules together with the pharmaceutical compound may be dispersed together in a suitable organic solvent and then mixed with aqueous medium; subsequent removal of the organic solvent causes formation of oligolamellar vesicles. These structures consist of a limited number of bilayer lamellae entrapping a disproportionately large volume of aqueous medium and hence of pharmaceutically active ingredient. One particular method of such type of encapsulating biologically active substances in synthetic oligolamellar lipid vesicles is described in British Patent Specification No. 2015464B to Papahadjopoulos et al.

An alternative method for encapsulating biologically active materials in synthetic oligolamellar lipid vesicles is disclosed in for example U.S. Pat. No 4,016,100 to Suzuki et al. This procedure has been devised because of the desirability of ensuring the sterility of pharmaceutical compositions of the aforesaid type and in particular minimising the amount of organic solvents present. It requires the dispersion of a phospholipid uniformly in water, adding a medicament to the aqueous dispersion of lipid spherules thus formed, freezing the medicament dispersion to entrap the medicament in the spherules and then thawing the frozen dispersion.

All of the processes hitherto described for production of vesicles for delivery of active ingredients have been directed to the provision of a mode of administration of water soluble active ingredients. In general these ingredients have been pharmaceutical substances, although Papahadjopoulos et al mentions the production of vesicles which may contain as active ingredients pesticides of various types. This disclosure, is to say the least, somewhat surprising because the vast majority of fungicides, insecticides, acaricides, nematocides and molluscicides encompassed by the term pesticide are at most only slightly soluble in water. Moreover for those that are soluble in water the problem then exists that for the compounds to be satisfactorily applied to plants, they must remain bioaccessible for a considerable time. Any pesticide in solution in water in a vesicle will normally be subject to the action of for example ultra-violet radiation and be subject to rapid degradation in the absence of measures designed to provide protection from these environmental hazards.

It is therefore an object of this invention to provide a spray method which may be applied to the full spectrum of pest control agents. It is a further object of the invention to provide a spray method which enables a substance to be applied to a surface to be retained thereon for an extended duration without undergoing degradation of its properties.

BRIEF DESCRIPTION OF THE INVENTION

According to one aspect of this invention, there is provided a wettable powder having the capacity for making up into a sprayable aqueous dispersion, which powder comprises an active agent to be employed at a target to be sprayed and which is not readily soluble in water, and a water-soluble naturally occurring organic product having the capacity to serve as a non-polar domain which has high affinity for hydrophobic molecules to keep them in a stable aqueous dispersion. The volume of the non-polar domain may be increased by inclusion of non-polar molecules such as organic oils and solvents such as glycerides, alkanes, alkenes etc., together with the aforesaid "organic product" e.g. amphipathic compound which is a source of surface-active molecules. By this means a stable oil-in-water emulsion is created which represents an extended reservoir for biologically active reagents to partition.

According to a second aspect of this invention, there is provided a method for the production of a wettable powder according to the first aspect of the invention, which comprises forming a mixture of the water-soluble organic product having the capacity to serve as a non-polar domain, the active ingredient and an organic solvent, agitating the mixture gently and removing the organic solvent.

According to a third aspect of the present invention, there is provided a method of applying to a substrate an active agent which is not readily soluble in water, which comprises incorporating the active agent in a wettable powder according to the first aspect of the invention, forming a dispersion of the wettable powder in an aqueous medium and applying the dispersion by spraying to a substrate on which the active agent is to be effective.

BRIEF DESCRIPTION OF THE FIGURES

FIG. 2b is a graphical depiction of the rainfall during the recovery period shown in FIG. 2a.

DETAILED DESCRIPTION OF THE INVENTION

Figure 1:
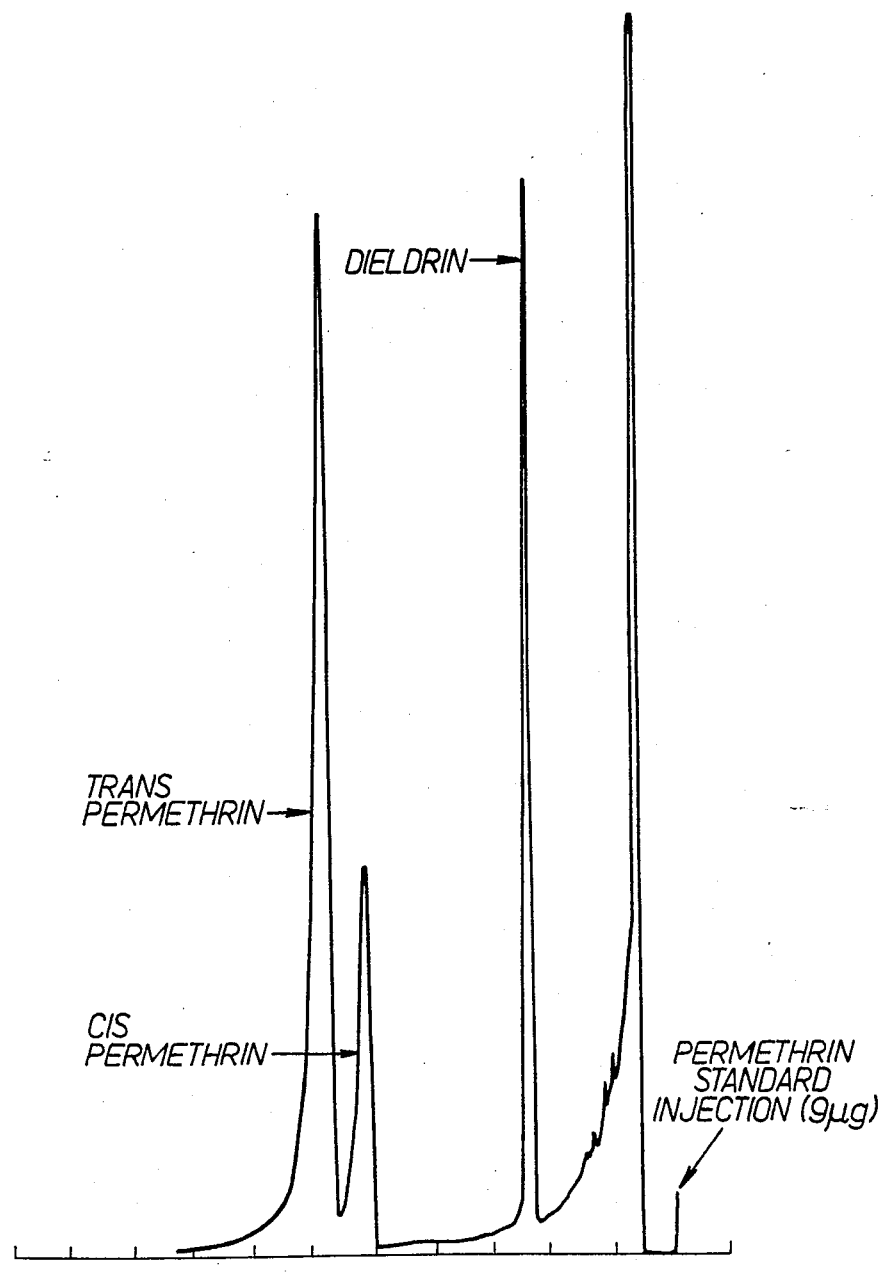
FIG. 1 depicts a chromatographic trace employed to analyze the persistence of permethrin applied by the present method.

The formulations of this invention may in principle be formed by the method described by Bangham et al in J.Mol. Biol., 13: 238-252 (1965) which involves dissolving the biologically-active agent and an amphipathic compound which is to serve as a domain for the active agent in a volatile organic solvent and removing the solvent by evaporation. At the time of application, an appropriate volume of an aqueous medium which will preferably be a salt solution containing, for example, from 5 to 250, preferably from 10 to 20 mM NaCl, is added to the wettable powder thus produced. Mechanical agitation results in the formation of a stable dispersion which can be sprayed using conventional equipment. This procedure is to be distinguished from that proposed by Papahadjopoulos which is aimed at producing a large volume of water-containing active ingredient entrapped within a vesicle. The procedure according to Bangham et al yields multilamellar (as against oligolamellar) lipid vesicles having a relatively small trapping volume. The desirability of a small trapping volume is best appreciated when it is realised that in general such active agents as pest control agents are not significantly water-soluble and cannot therefore be satisfactorily utilised in forming synthetic lipid vesicles according to Papahadjopoulos. Insofar as pest control agents are generally hydrophobic, it is now appreciated that provided an appreciable partition coefficient exists between the amphipathic compound and water for the pesticidal compound, then the pest control agent can be expected to partition into the hydrophobic domain created by the amphiphatic and non-polar molecules which then become the vector for the pest control or other biologically-active agent. In the case of lipid amphipaths, as the interior of the vesicles formed will then only contain water, it is undesirable that the vesicle interior should be large and hence the above-indicated method attributed to Bangham et al is preferred for forming the wettable powders of this invention.

As an alternative to using the method of Bangham et al, it is also possible, in principle, to employ the method of U.S. Pat. No. 4,016,100 in forming wettable powders of this invention. However, this is a more complicated procedure which is not necessary when producing pest control formulations where the need for more stringent precautions to produce a sterile composition does not arise.

In general, it has been found that the presence of a small amount of an organic solvent added at the time of making up the composition to be sprayed assists in the stability of the emulsion/dispersion produced for spraying. Examples of solvents will be given hereinafter.

A significant difference in practice between the method to be employed derived from the teachings of Bangham et al in producing the sprayable dispersions in the method of this invention and the method for producing dispersions according to Papahadjopoulos is that since Papahadjopoulos requires the existence of a relatively large volume of trapped aqueous solution, a particularly vigorous mechanical agitation step e.g. ultrasonic irradiation is carried out to produce a homogeneous emulsion. In contrast, when producing the sprayable composition for use in the method of this invention with only a minimum amount of entrapped aqueous solvent relatively gentle mechanical agitation conditions are contemplated as will be apparent from the Examples which follow.

One method of producing the wettable powders is to use organic solvents to produce an intimate mixture of organic products having the capacity to serve as a non-polar domain, preferably a phospholipid, and active ingredient and to remove the solvent to create a wettable powder. Examples of solvents which may be used at this stage and also when making up a composition to be sprayed are alcohols such as methanol ethanol, propanol, butanol, pentanol and higher alcohols, ethylene glycol, xylene, dioxane, dimethylformamide acetone and chloroform. The agitation can be relatively gentle, for example by stirring with a food mixer mechanism, in contrast to conventional procedures which involve use of sonication. These procedures are in contrast to that of Paphadjopoulos in which the organic solent is present during the dispersion forming step in all cases, which step requires vigorous agitation, and is *required* for formation of oligolamellar vesicles.

A variety of water-soluble organic molecules satisfies the criterion of acting as a solvent vector in that such molecules are amphipathic and incorporate hydrophobic domains providing high affinity for pesticides and other molecules of low solubility in water. Emulsification in this case can be achieved simply by adding the water-soluble amphipath to a dry preparation of biologically active compound or other reagent. Examples of suitable raw materials which may be mentioned are denatured collagen, egg albumen and soya and fish products. Although the amphipaths will generally be proteins, it is not essential that their sources be of purely proteinaceous nature, as in the case for example of mucopolysaccharides. However, it may be expected that the higher the polysaccharide content, the lower will be the affinity of the naturally occurring material for hydrophobic molecules and generally some modification of the structure will be required, as for example by attaching active groups to the clathrate structure of the mucopolysaccharide. A particularly inexpensive and readily available material to use is, however, soya lecithin. Soya lecithin is in fact a mixture of phosphatidylcholines, phosphatidylethanolamines, phosphatidylserines and phosphatidylinositols each of which classes consists of a range of molecular species characterized by the acylation to fatty acids of a different length, number and position of unsaturated carbon-carbon double bonds and position of attachment, C1 or C2, of the glycerol molecule. Grades of soya lecithin available commercially are rated according to the amount of soya oil remaining in the acetone insoluble fraction in which the lecithin is obtained from the product of soya bean crushing. The more refined extracts are also available as water-disperible lecithin, granular lecithin and lecithin powder. In fact, it is sufficient to use a crude grade of lecithin in the practice of this invention.

The compositions of this invention may contain a wide variety of pest control agents. These may be fungicides, insecticides, acaricides, nematocides or molluscicides. Of particular interest are pyrethrin insecticides, for example Cypermethrin, Deltamethrin and Permethrin. However it is also possible to employ for example carbamate and organophosphorus compounds. Specific examples of further pest control agents within the aforesaid headings which may be employed in the practice of this invention are the following:

| Insecticides | Fungicides | Acaricides |
|---|---|---|
| Chlorpyrifos | Benomyl | Amitraz |
| Demeton-S—methyl | Binapacryl | Azinophos-methyl |
| Dicofol, | Captan | Diazinon, |
| Diflubenzuron, | Carbendazim, | |
| Dimethoate | Chlorothalonil | |
| Iodofenphos, | Cufraneb | |
| Iprodione, | Dichlorfluanid | |
| Malathion, | Imazalil, | |
| Mephosfolan, | Triadimenol | |
| Permethrate, | Triadimefon | |
| Pirimicarb, | Triforine | |
| Tetradifon, | Dinocap | |
| | Etridiazole, | |
| | Maneb, | |

-continued

| | |
|---|---|
| Metalaxyl, | |
| Propioconazole, | |
| Nematocides | Molluscicides |
| Aldicarb, | Methiocarb. |
| Dichloropropene, | |

In addition to or as an alternative to containing pest control agents, the wettable powders may contain herbicidal agents which have relatively low solubility in aqueous media. Specific examples of herbicidal agents include, Benzoylprop-ethyl, Flamprop, Atrazine, Aziprotryne, Bromacil, Carbetamide, Chlorbromuron, Chloridazon, Chlorthal-Dimethyl, Diphenamid, Diuron, Lenacil, Linuron, Metamitron, Methabenzthiazuron, Methazole, Metribuzin, Propham, Propyzamide, Simazine, Terbacil and Trietazine.

There is preferably is included in the wettable powder an ultra-violet absorbent. There are a wide variety of available ultra-violet absorbents among which may be mentioned by way of example only the substances commercially available under the family names of Uvinul, Aduvex, and Tinuvins. In general suitable UV-absorbents are organic compounds, insoluble in water but soluble in non-polar solvents. Thus when producing the wettable powders, these compounds will partition into the naturally occurring organic product which will be termed hereinafter "the phospholipid" although as indicated above this invention can use a broader range of organic compounds, since they possess a satisfactory partition coefficient between an organic phase and water so as to remain in the organic phase during spraying. This means that the sprayed bilayer-forming material will possess, in intimate association with each other the pest control agent and an ultra-violet absorbent. In this way the effective life of the applied composition will be considerably extended in general allowing the pest control and herbicidal agents to remain active on a plant surface as long as required, subject to avoidance of washing off.

Insofar as the long effective life of the wettable powders which made possible by the presence of ultra-violet absorbents is conderned, this enables spray formulations to contain more than one pest control agent which partition into the phospholipid so that either or both of the following phenomena may be achieved. Firstly it becomes possible to incorporate and apply by a single spraying a combination of compounds which are to be effective on pests at a different stage in the growth cycle of either the pest or of the plant. The active ingredients will thus lie side by side in the liposome and act when appropriate. Indeed by having the pest control agents available in such manner it is possible that, secondly, they act together, often synergistically, to provide an enhanced effect at appropriate stages in plant growth. The action of the spray formulations produced from the wettable powders of this invention is to be distinguished from any action which would be achieved with the aforementioned formulations of Papahadjopoulos containing pest control agents restricted to the aqueous compartment of the formulation.

It is generally desirable that the applied formulation be retained upon a plant for as long as possible. Because of their polar outer surfaces, liposomes are generally suited to this and are certainly far superior in performance to detergents as already mentioned herein. Hence the controlled release characteristics together with the continuing retention on a plant surface make the formulations of this invention particularly valuable weapons in pest control. Furthermore, the wettability, dispersibility, adhesiveness, resilience etc., properties of the amphipathic vector system can be modulated to particular plant systems or environmental conditions by adjustment of the surface electrostatic charge of the liposome structures. Thus, acidic phospholipids or long chain fatty acids would impart a net negative zeta potential to the lipid vector.

The wettable powders may contain additional components to those already mentioned herein. Examples of substances which may be employed in this way are free radical quenchers such as butylated hydroxy toluene and tocopherol and pheromones or other bait attractants. Again these substances are preferentially taken up in the hydrophobic domain formed by a phospholipid whether or not it contains additional non-polar material. Bait attractants have hitherto been proposed for use with viral pest control agents such as Heliothis virescens used in the conventional method hitherto employed. Here, the bait normally consists of a commercial cotton seed adjuvant (the product CoAX, produced by Traders Oil Mill Co., Forth Worth, Tex.) and the application is by aqueous solvents, there having been proposed for this purpose an application rate of 140 liters water/hectare and a pressure of 276 KPa achieved with $CO_2$ gas pressure (see J. Econ. Entomol, 76, 446–448, 1983). An advantage of the use of pheromone traps in liposome formulations embodying this invention is that the sex attractant will be released at a much more controllable rate from phospholipid bilayers, especially compared with the release rates from capillary tubes or Pheracon rubber septa impregnated with the pheromone as had been the case with all pheromone baited traps currently marketed.

Although the invention has been described here primarily with respect to the spraying of plants, in general it is applicable to the spraying of pest habitats and hence, subject to the avoidance of too rapid a liposome breakdown, may be extended to the spraying of ground areas which constitute habitats for pests.

In addition this invention may be applied to the protection against attack by pests of plant products and clothing. Thus the formulations of this invention may contain as active ingredient the synthetic juvenile hormone analogue, Methoprene, which is known to prevent larval forms of the cigarette beetle and tobacco moth from developing into normal pupae or adults. When this material has hitherto been applied to tobacco materials in an ethanol:water solvent (10 ppm active ingredient) protection has been provided for stored tobacco material for four years. The invention finds application in sprays (generally pressurised sprays) of insecticides such as Permethrin in particular, to be applied to clothing for personal protection against ticks. The application of a Permethrin formulation according to the present invention to clothing provides the Permethrin on the clothing for the length of time the clothing is being worn, that is up to the next washing; during such time, there will be protection against these ticks.

A further type of pest control to which this invention may be applied is in the protection of stored cereal grains. Hitherto it has been proposed that petrol-ether extracts of tumeric rhizomes, neem or funugreet leaves give effective protection against the different pests affecting stored grain. The active ingredients of these extracts can be conveniently transferred to a phospholipid phase in a formulation according to this invention for reliable application to stored grain.

Whilst this invention has been described herein primarily with regard to a variety of formulations for pest control, it is of more general use in that it can be employed whenever there is a requirement for the delivery to a surface of an active ingredient which partitions preferentially into an organic phase from a mixture of organic phase and water. The application of herbicidal agents to plants, for example, can also be usefully performed using the invention described. Like most pesticidal agents, most herbicides in current use are relatively insoluble in water and unstable to ultraviolet light. The liposomal vector system into which ultraviolet absorbing molecules are incorporated serves to stabilize herbicidal agents in the same manner as described for pesticidal agents. Although, this invention can be used to apply herbicidal agents to growing plants, because of the continuing bioavailability which it provides especially when UV protecting agents are included, it is particularly suitable for spraying of newly sown ground to prevent establishment of growth of weeds over an extended period of time not possible with conventionally applied herbicides.

There now follows a series of experiments carried out to determine typically optimum sprayable compositions embodying this invention:

EXPERIMENT 1

Comparison of different amphipaths in their ability to form stable emulsions in water Several sources of amphipathic molecules of biological origin suitable for development as pesticide or herbicide vectors were examined for their ability to form stable emulsions. Dispersions of the following compounds were prepared in water and a neutral plant pigment extract was added as a colour indicator to observe settling and phase separation within the dispersion.

1. Egg albumin, 2.5 g per liter
2. Egg albumin, 5.0 g per liter
3. Total polar lipid extract of bean leaves, 5.0 g per liter
4. Soya lecithin (Sigma, London) 2.5 g per liter
5. Soya lecithin (Sigma, London) 5.0 g per liter.

Egg albumin was dispersed directly in water; lipid preparations were dried from organic solvent (chloroform) and dispersed mechanically according to Bangham et al.

The dispersions which were formed in this way were allowed to stand undisturbed and were photographed periodically to follow settling out. The soya lecithin dispersions were found to be the most stable and indeed when not combined with plant pigment, even greater stability was observed. Significantly improved stability was also achieved by using 5 to 20 mM NaCl to replace water as the solvent.

EXPERIMENT 2

Testing of the stability of soya lecithin dispersion

Several soya lecithin dispersions were made up each containing a small amount of lipid soluble anthraquinone dye to serve as a marker. An optical density reading was taken for each dispersion. These emulsions were then centrifuged at 2000 g for 10 minutes to speed up settling and another optical density reading was taken. The optical density readings were used to calculate the amount of lipid remaining in suspension from which the percentage settling could be calculated.

The emulsions varied in their method of dispersion and the presence or absence of 20 mM NaCl as set out in the following Table 1:

TABLE 1

| Sample No. | Method of dispersion | Salt | % settled out |
|---|---|---|---|
| 1 | Vortex mixed | − | 83 |
| 2 | Vortex mixed | + | 16 |
| 3 | Sonicated | − | 11 |
| 4 | Sonicated | + | 0 |

It was because of the conclusions which could be drawn from the above Table that in subsequent work there was used soya lecithin dispersion made up in 20 mM NaCl solution using a sonicator. Subsequent experiments using a domestic food mixer produced a dispersion of soya lecithin in 20 mM NaCl that was completely stable to centrifugation at 2000 g for 10 min. This method was subsequently employed for further tests of the formaulation.

EXPERIMENT 3

Determination of the amount of liposome vector delivered and persisting on leaves (a) Determination of the efficiency of chloroform extraction of dye from water To undertake this experiment it was necessary to device a method for quantitative extraction of marker dye (anthraquinone) from spray formulations and residues removed from sprayed leaves by water washing.

Four aliquots (100 μl) of a dispersion of soya lecithin containing dye were pipetted into known amounts of water and 10 ml of chloroform were added. A further aliquot (100 μl) of dispersion was pipetted directly into 10 ml of chloroform. The efficiency of the extraction method was calculated by relating the amount of lipid extracted from each of the aqueous samples to the amount of lipid pipetted directly into chloroform. The results are set out in Table 2.

TABLE 2

| Sample No. | % Lipid recovered |
|---|---|
| 1 | 90 |
| 2 | 77 |
| 3 | 77 |
| 4 | 98 |

This gives an average recovery value of 85.5%. Varying ratios of chloroform and water were examined and the most effective was found to be 50 ml of water to 10 ml of chloroform. This test provides a useful way to determining the most efficient partitioning into an organic solvent and can be readily repeated using cheaper organic solvents for commercial use. The method may also be used to monitor the distribution and/or persistance of the liposomal spray formulation to plant material and with analyses of biologically active agent residues provides a useful index of biological persistance.

(b) Effect of concentration of amphiphath in spray formulation on leaf retention Dispersions of soya lecithin containing marker dye were made up with varying concentrations of lipid in the range of 2.5 to 100 g/l. A number of leaves were sprayed with dispersions of each concentration using an ASL Spraymist garden sprayer and then placed in a drying cabinet. Leaves were removed at hourly intervals, dipped three times in 50 ml of water and then placed in 10 ml of chloroform. 10 ml of chloroform were added to the water extracts and the water/chloroform and chloroform samples were both left for 15 minutes. Optical density readings were taken for both the chloroform fractions to measure dye concentrations and the amount of lipid in each was calculated. These figures were used to calculate the percentage lipid washed off. The results obtained are shown in Table 3.

TABLE 3

| Lipid concentration | Percentage lipid washed off-range | Average |
|---|---|---|
| 100 g/l | 17–28 | 21% |
| 60 g/l | 27–42 | 38% |
| 30 g/l | 23–34 | 29% |
| 10 g/l | 34–47 | 42% |
| 2.5 g/l | 26–58 | 42% |

Some of the 60 g/l results were affected by a slight increase in drying cabinet temperature, but overall it was clear that more of the soya lecithin emulsion is retained on the leaf as the concentration in the spray formulation is increased. This indicates that the liposomal vector system will be highly suited to high concentration-low volume applications of pesticides and herbicides to crop plants.

Comparative tests were carried out with several commercially available pesticide compositions made up according to manufacturers instructions and used in tests similar to those outlined above. Dye was added to these in appropriate concentrations. The results obtained are set out in the following Table 4.

TABLE 4

| Name | Percentage lipid washed off-range | Average |
|---|---|---|
| Malathion | 32–52 | 41% |
| Spring spray | 37–47 | 43% |
| Spray day | 38–50 | 45% |
| Liquid Derris | 25–36 | 30% |

These results show clearly that the soya lecithin liposome formulation in concentrations greater than 10 g per liter is retained more persistently on bean leaves subjected to a water wash than the commercially available formulations examined.

EXPERIMENT 4

Trials with Permethrin

A basic dispersion was made up by the method of Bangham et al, consisting of 3 g of soya lecithin, 0.1 g of an insecticide, Permethrin, and 100 ml of 10 mM NaCl to give 1 mole of Permethrin per 15 moles of phospholipid. This composition was found to show high retention on leaves subjected to washing after application of the lipid dispersion by the method described in Experiment 3(b), a high stability as judged by absence of a sediment after centrifuging for 10 min. at 2000 g and from settling studies performed over a 5 month period. The formulation contained a sufficient amount of Permethrin to kill most insects.

The following experiments were then carried out:

a. Residue persistence

In this experiment reference is made to analysis by gas chromatography. This chromatography was performed on a GVC gas chromatograph using a 2.8 m×0.4 cm column packed with a stationary phase of Chromosorb W AW DMCS (80–100 mesh size) coated with 5% (w/w) OV 210. the oven temperature was 230° C. and the injection and detector chambers were maintained at 250° C. The carrier gas was nitrogen adjusted to a flow rate of 42.5 ml.min$^{-1}$. The permethrin concentration was determined from the peak of an internal standard of dieldrin using an electron capture detection system. A typical chromatrogram is shown in FIG. 1 of the accompanying drawings.

Figure 2A:
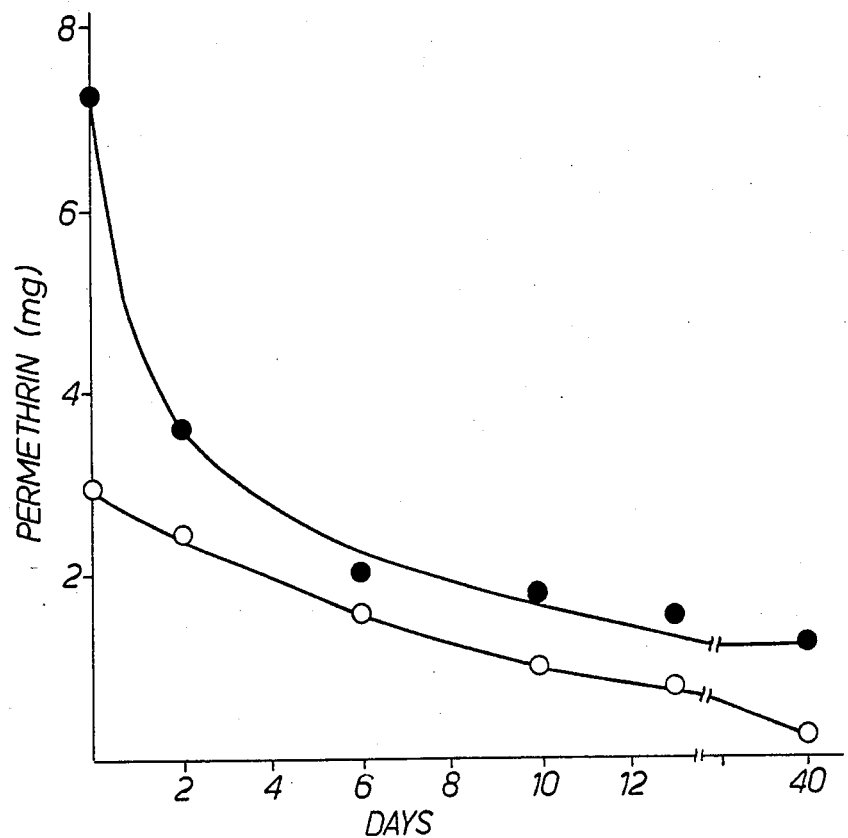
FIG. 2a is a graphic depiction of the comparative recovery of permethrin applied to plants by the pesent method.
Figure 2B:
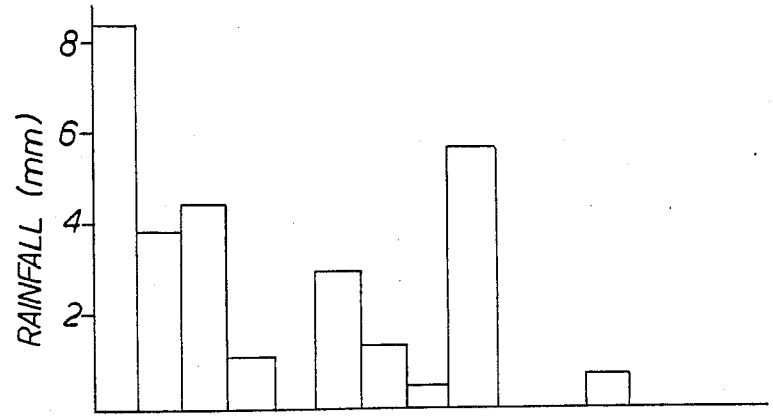

A trial of the residue persistence of the formulation of permethrin in soya lecithin was conducted on pea plants, 30–40 cm in height, under field conditions. The behaviour of the formulation was compared with that of a commercial wettable powder formulation, Coopex, Registered Trade Mark of the Wellcome Foundation, which was applied according to the manufacturers instructions. Blocks of 4 pots with 3 plants per pot were sprayed to "run off" with 42.5 ml of spray formulation using a pressure atomiser spray device. The lecithin formulation showed much better leaf coverage than Coopex with which there was a tendency for droplets of high contact angle to form on the leaf surfaces. This left a blotched effect with concentrations of a white powder on the leaf surface whereas the lecithin-containing treatments were sticky in appearance. Sprayed plants were held in the laboratory for 24 hours and then placed in an exposed position on the roof of the laboratory. At each time-point, blocks of plants, 12 plants in each block, treated with the two formulations respectively were removed and extracted with 700 ml chloroform for 30 min. The extract was evaporated to dryness and redissolved in 50 ml chloroform and finally dried under $N_2$. The dried extracts were redissolved in 10 ml of diethylether containing an internal standard of dieldrin. An aliquot of 1 ml was diluted ×10 in diethyl ether and 2 ml were analysed by gas chromatography as described above. The results are presented in FIG. 2a of the accompanying drawings in which the solid circles indicate permethrin residues recovered from pea plants and the open circles denote Coopex recovered from pea plants (24 per treatment). Rainfall recorded during the trial is shown above in FIG. 2b which uses the same abcissae. The results show that the residues of permethrin retained on the foliage were much greater throughout the 40 day trial with the lecithin formulation. In quantitative terms the residue after 40 days with the lecithin formulation was almost identical to the Coopex spray after 6 days.

b. Aerosol properties

Figure 3A:
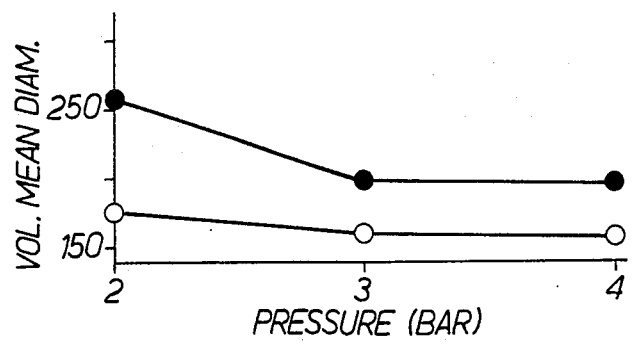
FIGS. 3a-3d graphically depict the effect of lecithin on the spray characteristics of an aqueous emulsion of a cereal fungicide.
Figure 3B:
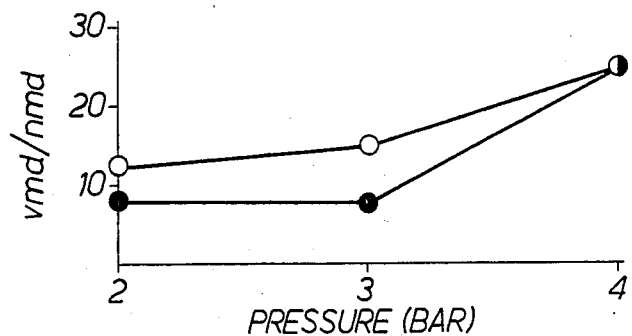
Figure 3C:
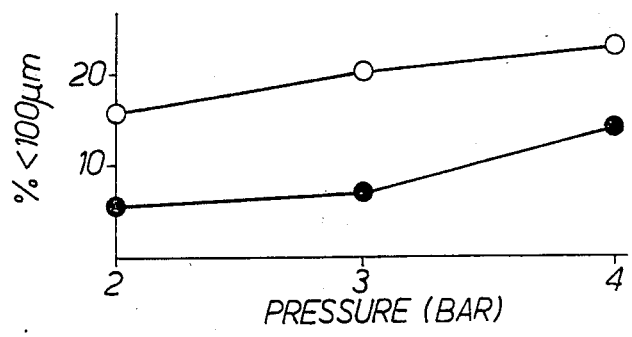
Figure 3D:
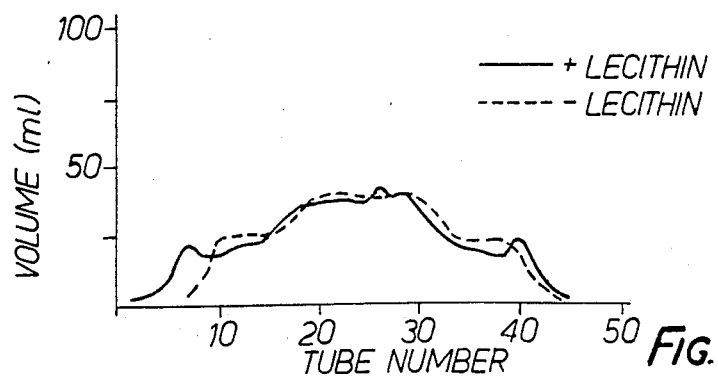

The spray characteristics of a commercial formulation of the cereal fungicide, propioconazole, available under the Registered Trade Marks Radar and Tilt, were examined using a Malvern particle size analyser and a pattenator to determine the effects of soya lecithin. An emulsifiable concentrate of Radar was diluted 2.5 ml per 1 of water and the spray characteristics were determined in the presence and absence of 5 g per 1 of lecithin (equivalent to an application rate of 1 Kg per ha). The results presented in FIG. 3 of the accompanying drawings show that, at pressures over the range 2 to 4 Bar with a 110° fan nozzle, the presence of lecithin significantly increased the volume mean diameter (FIG. 3a) and reduced the ratio of volume:number mean diameter of the particles (FIG. 3b) and reduced the percent of droplets with a diameter of less than 100 m (FIG. 3c). The droplet characteristics of Radar are similar to water and the effect of the soya lecithin dispersion on the Radar formulation is the same as that when added alone to water. The distribution of spray was examined in a pattenator at 2 Bar pressure (FIG. 3d) and the presence of lecithin in the Radar formulation was seen to cause a more even and wider distribution of the droplets consistent with the effects of lecithin on droplet characteristics.

EXPERIMENT 5

Dispersion stability of formulations containing UV absorbers

In order to determine the dispersion stability of a dispersion formulation of the type used in Experiment 4, soya lecithin was dispersed in combination with Permethrin and a typical UV absorber Tinuvin. The supernatants and precipitates were assayed for inorganic phosphate arising from the soya lecithin and subjected to gas chromatographic analysis for estimation of Permethrin and Tinuvin. The formulation employed contained 300 mg of soya lecithin in 10 ml of 10 mM NaCl. This concentration had previously been found to give maximum adhesion to plant leaves when employing the water dipping test described in Experiment 3(b). The Permethrin added was in a final concentration of 10 mg/ml. This concentration was found to be highly effective as an insecticide agent in an aerosol formulation. Tinuvin was present in a concentration of 20 mg/10 ml. This quantity was chosen in order that there should be approximately 5 mol of Tinuvin/mol of permethrin.

The soya lecithin employed had contained only about 63% of phospholipid of which phosphorus represented about 4%. As no obvious trace of solvent could be detected, the likely contaminant was believed to be glycerides a fact consistent with a quantitative analysis of total fatty acid methyl esters by gas chromatography.

Using this soya lecithin, it was observed that a stable dispersion could be achieved using mechanical methods (domestic food mixer) as determined by analyses of supernatant and precipitating fractions resulting from centrifugation for 10 min. at 2000 g. As can be seen from the results presented in Table 5 Permethrin partitions entirely into the phospholipid phase irrespective of whether Tinuvin was present or not. Only about 40% of the Tinuvin partitions into the lipid to form a constituent of the emulsion. The remaining Tinuvin forms a precipitate.

TABLE 5

| Constituents (mg/10 ml) | mg* | | | | | | | |
|---|---|---|---|---|---|---|---|---|
| | 1 | | 2 | | 3 | | 4 | |
| | dispersed | ppt | dispersed | ppt | dispersed | ppt | dispersed | ppt |
| Soya lecithin (300) | 124 | 50 | 180 | 21 | 161 | 30 | 184 | 4 |
| Permethrin (10) | — | — | 9.4 | 1.1 | — | — | 9.6 | 0 |
| Tinuvin (20) | — | — | — | — | 4.7 | 15.7 | 6.1 | 15.2 | values represent a mean of two experiments

A variety of other ultra violet absorbing reagents were tested in the formulation as described for Tinuvin including different members of the Uvinul and Aduvex groups of compounds and their successful incorporation into the liposomal vector was successfully demonstrated. In practice, appropriate ultraviolet stabilizing reagents can be selected according to the particular sensitivity of the pesticidal or herbicidal agent(s) representing the biologically active component(s) of the formulation. It should be noted that in most cases screening of light of wavelengths utilised for photosynthesis is avoided.

EXPERIMENT 6

Stability of Permethrin formulation to UV radiation

Holmstead et al have reported in J.Agric.Food Chem. (1978), 26, 590–595 a rapid degradation of Permethrin, especially the cis isomer on exposure to UV light in the spectral region of =290–320 nm. These results were based on experiments in which 10 mM solutions of Permethrin in organic solvents were exposed to UV light and not under conditions simulating their deposition on plant foliage. It was found that degradation was prevented by some UV absorbers but not others even at concentrations of 50 fold molar excess over the pesticide. Successful protection was found to depend on the relative spectral features of Permethrin and the particular UV absorber.

In order to test the stability of Permethrin in soya lecithin in a layer on a surface, exposure to UV light was effected in a formulation similar to that given in Experiment 5. The effect of inclusion of the UV absorber Uvinul-D49 was also checked. When Uvinul was present, it was in a ratio of 3 moles of Uvinul per mole of Permethrin. The spray formulation was dried onto aluminium discs (2.5 diameter) and exposed to a strong ultraviolet source for different periods of time and the residues were subsequently analysed by gas chromatography as described in Experiment 4. The results of the analyses are presented in Table 6 and the values were quantitated from an internal reference of octacosane.

TABLE 6

The effect of Uvinul-D49 on the degradation of Permethrin present in a dried liposomal preparation subjected to ultraviolet irradiation.

| UV Exposure Time (mins) | Uvinul D49 | Octacosane reference | PEAK AREA Cis Isomer + Uvinul D49 | Trans Isomer | Trans octacosane |
|---|---|---|---|---|---|
| 0 | — | 1.717 | .514 | 1.989 | 1.16 |
|   | + | 1.505 | .793 | 1.68 | 1.12 |
| 1.5 | — | 1.947 | .32 | 1.079 | .554 |
|   | + | 1.645 | .804 | 1.57 | .954 |
| 3 | — | 1.912 | .279 | .939 | .491 |
|   | + | 1.707 | .779 | 1.332 | .780 |
| 4.5 | — | 2.007 | .217 | .63 | .314 |
|   | + | 1.766 | .638 | .974 | .551 |
| 6 | — | 1.648 | .181 | .584 | .354 |
|   | + | 1.94 | .657 | .925 | .477 |

Permethrin remaining was calculated using only the data from the trans isomeric peak curve as Uvinul-D49 interferes with the cis peak.

Figure 4:
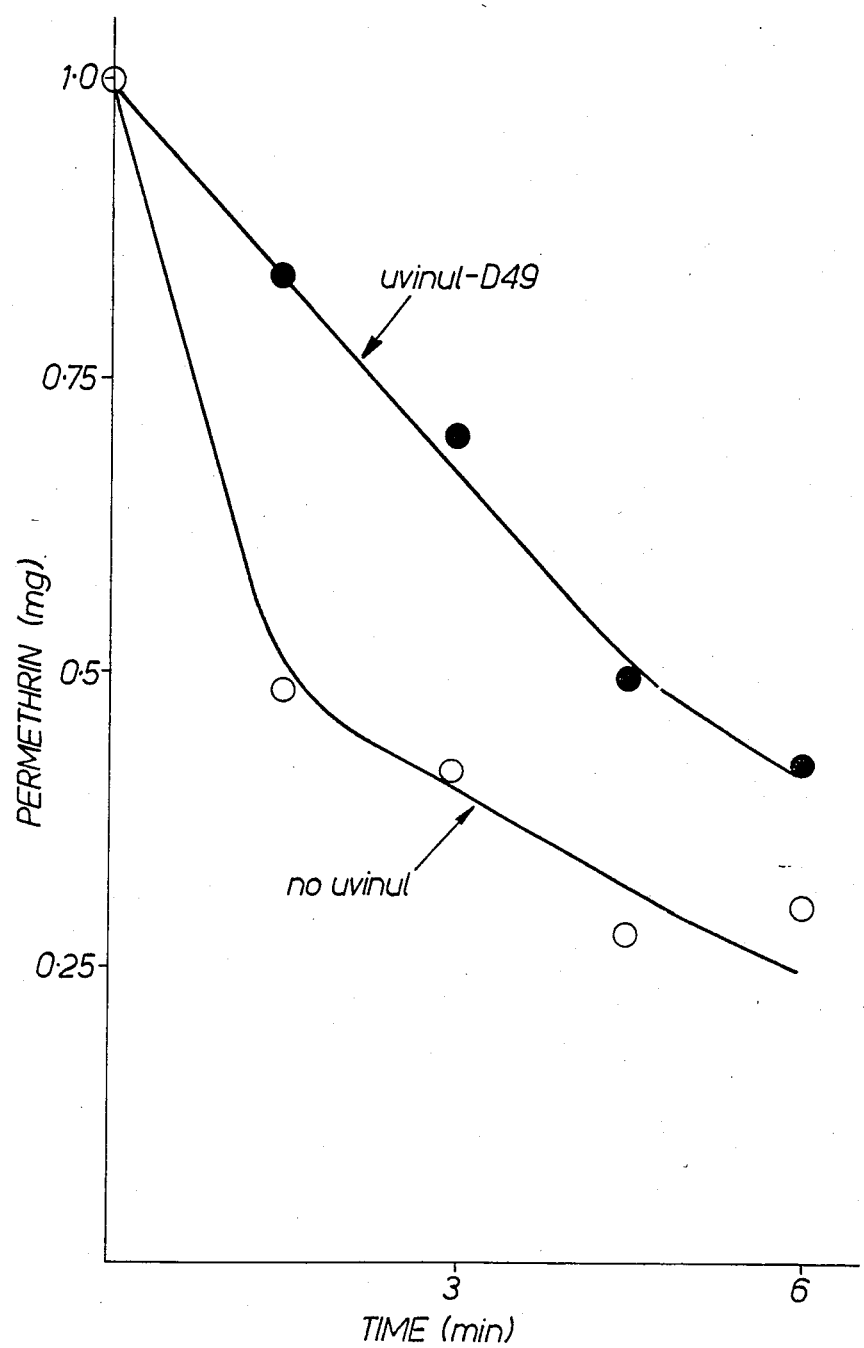
FIG. 4 is a graphic depiction of the rate of degradation of permethrin in the presence and absence of a UV absorber.

A comparison of the peak heights of cis and trans Permethrin with the internal reference of octacosane showed that exposure to UV light causes considerable decrease in the presence of the cis and trans isomers of Permethrin and the effect of the cis isomers is greater than on the trans isomers. Uvinul is also degraded on exposure to UV light, but in the concentration used provided significant protection against degradation of the two isomers of Permethrin. A graphical illustration of the amount of Permethrin remaining as a function of time of exposure to ultraviolet irradiation is given in the FIG. 4 of the accompanying drawings. This shows conclusively that the presence of Uvinul-D49 in the liposomal formulation provided significant protection against degradation of the Permethrin.

Subsequent experiments have been carried out to yield equivalent results for:

1. Conventional commercially available Permethrin preparations which, in general, do not contain stabilisers against UV degradation. This is believed to be due to the short bioavailability of Permethrin on plants associated with relatively rapid wash-off of Permethrin.
2. Conventional commercially available Permethrin preparations to which had been added stabilisers against UV degradation, including Uvinul-D49.
3. Permethrin formulations according to this invention, from which stabilisers against UV degradation were omitted.
4. Permethrin formulations accoring to this invention additionally containing stabilisers against UV degradation.

It was observed that the stability of formulation 3 was generally greater than that of formulation 2 despite the absence of a UV stabiliser and that overall the stability of the formulations was in the order: 4>3>2>1.

What is claimed is:

1. A method of applying to a substrate a hydrophobic pesticidal or herbicidal agent which is not readily soluble in water and which is to be effective at the substrate, which comprises:
   (a) mixing the hydrophobic agent with a water-soluble, naturally occurring amphipathic organic compound to form a wettable powder;
   (b) mixing said wettable powder with an aqueous medium to form a stable aqueous liposomal dispersion consisting essentially of water, the amphipathic organic compound and the hydrophobic agent; wherein the organic compound includes a non-polar domain which exhibits a high affinity for said hydrophobic agent; and
   (c) spraying said aqueous dispersion onto the substrate.

2. The method of claim 1, wherein said organic compound is a phospholipid amphipath.

3. The method of claim 1, wherein said organic compound is denatured collagen, egg albumin, a seaweed extract, a soya product or a fish product.

4. The method of claim 3, wherein said organic compound is soya lecithin.

5. The method of claim 1, wherein the agent is a fungicide, insecticide, acaricide, nematocide or molluscicide.

6. The method of claim 5, wherein the insecticide is a pyrethrin.

7. The method of claim 1, wherein the powder includes an ultra-violt absorbent which is insoluble in water but is soluble in a non-polar solvent.

8. The method of claim 1, wherein the powder additionally contains a free radical quencher.

9. The method of claim 1, wherein the powder additionally contains a pheromone or bait attractant.

10. The method of claim 1, wherein the water further contains from 5 to 250 mM NaCl.

11. The method of claim 10, wherein the water further contains from 10 to 20 mM NaCl.

* * * * *

UNITED STATES PATENT AND TRADEMARK OFFICE
CERTIFICATE OF CORRECTION

PATENT NO. : 4,666,747
DATED : May 19, 1987
INVENTOR(S) : Peter J. Quinn

It is certified that error appears in the above-identified patent and that said Letters Patent is hereby corrected as shown below:

At Col. 5, line 17, for "collagen, egg albumen and soya" read --collagen, seaweed, egg albumen and soya--.

At Col. 6, line 44, for "is conderned, this" read --is concerned, this--.

At Col. 7, line 65, for "or funugreet leaves" read --or fenugreet leaves--.

At Col. 9, line 31, for "device a method" read --devise a method--.

At Col. 9, lines 53-54, for "way to determining" read --way of determining--.

At Col. 14, line 6, for "formulation provided significant" read --formulation provides significant--.

Signed and Sealed this

Twentieth Day of October, 1987

Attest:

DONALD J. QUIGG

Attesting Officer

Commissioner of Patents and Trademarks